United States Patent [19]

Callahan

[11] Patent Number: 5,449,376

[45] Date of Patent: Sep. 12, 1995

[54] SYSTEM AND METHOD FOR PRODUCING HIGHLY AMPLIFIED RADIO SIGNALS FOR FEEDBACK INTO THE HUMAN BODY

[75] Inventor: Philip S. Callahan, Gainesville, Fla.

[73] Assignee: Richard J. Fox, Wayne, Pa.

[21] Appl. No.: 77,389

[22] Filed: Jun. 17, 1993

[51] Int. Cl.⁶ .............................................. A61N 1/40
[52] U.S. Cl. ....................................................... 607/2
[58] Field of Search ................... 607/1, 2, 76; 361/216, 361/231, 232

[56] References Cited

U.S. PATENT DOCUMENTS

| | | | |
|---|---|---|---|
| 587,237 | 7/1897 | Sanche | 607/1 |
| 668,661 | 2/1901 | Schneider | 607/1 |
| 2,004,751 | 6/1935 | Fischer et al. | 607/68 |
| 5,010,777 | 4/1991 | Yehl et al. | 361/231 |

FOREIGN PATENT DOCUMENTS

| | | | |
|---|---|---|---|
| 0127680 | 4/1932 | Austria | 607/2 |
| 2006031 | 3/1969 | France | 607/2 |
| 2580180 | 10/1986 | France | 607/1 |
| 3607514 | 9/1986 | Germany | 607/1 |
| 3823178 | 1/1990 | Germany | 607/1 |
| 3900652 | 7/1990 | Germany | 607/1 |
| 0405912 | 2/1934 | United Kingdom | 604/20 |
| 0919338 | 2/1963 | United Kingdom | 607/2 |
| 1167053 | 10/1969 | United Kingdom | 607/2 |

Primary Examiner—William E. Kamm
Attorney, Agent, or Firm—Sterne, Kessler, Goldstein & Fox

[57] ABSTRACT

The present invention includes an apparatus and method for generating, duplicating, and transmitting biophotonic radio frequencies that propagate along the atmospheric boundary layer of the human skin and the earth's atmosphere. These biophotonic radio frequencies are applied to a human patient for therapeutic purposes. This function is realized with the use of a series of oscillators (i.e., electronic function generators) designed to produce modulated or unmodulated sine and square wave photons. The oscillators are further adapted to emit the modulated or unmodulated sine and square wave photons from a dielectric or metal antenna built as loops into the walls of a diamagnetic-paramagnetic chamber. When a person is seated in the chamber, the photons of energy from the waves generated along the loop antenna penetrate the human body and provide a variety of therapeutic benefits. Among these therapeutic benefits are relief of rheumatic muscular pain, slowing the metabolism, increasing the efficiency of the immune system, eliminating certain psychosomatic ailments, and suppressing cancer.

18 Claims, 5 Drawing Sheets

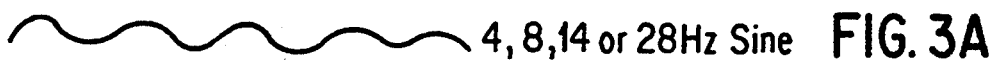
4, 8, 14 or 28 Hz Sine   FIG. 3A
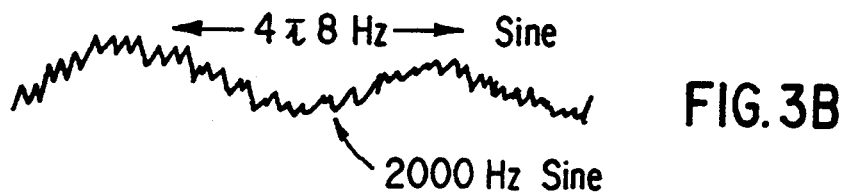
← 4 τ 8 Hz → Sine
2000 Hz Sine   FIG. 3B
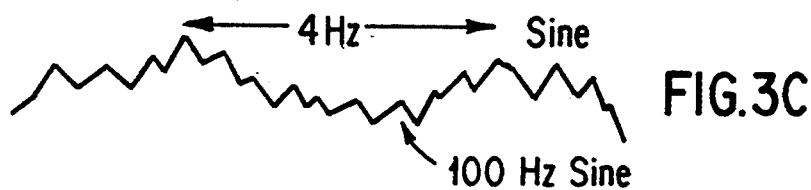
← 4 Hz → Sine
100 Hz Sine   FIG. 3C
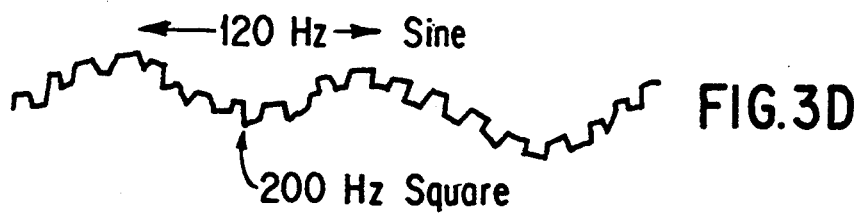
← 120 Hz → Sine
200 Hz Square   FIG. 3D
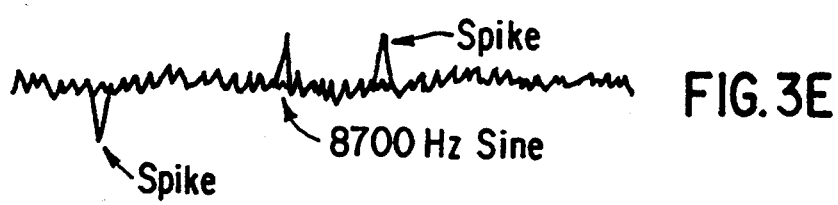
Spike
8700 Hz Sine
Spike   FIG. 3E
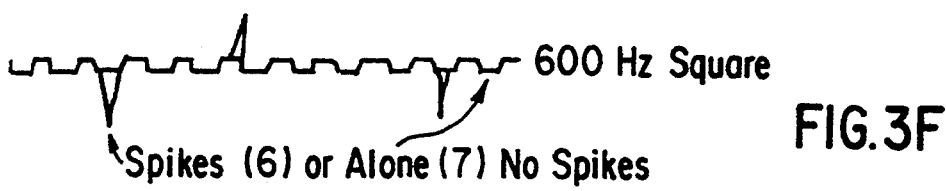
600 Hz Square
Spikes (6) or Alone (7) No Spikes   FIG. 3F
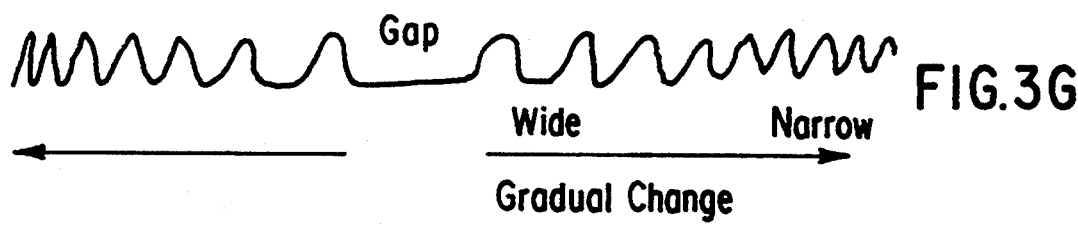
Gap
Wide   Narrow
Gradual Change   FIG. 3G

SYSTEM AND METHOD FOR PRODUCING HIGHLY AMPLIFIED RADIO SIGNALS FOR FEEDBACK INTO THE HUMAN BODY

BACKGROUND OF THE INVENTION

1. Field of the Invention

The present invention relates generally to an electronic photonic method and apparatus for using natural radio frequencies for therapeutic purposes, and more particularly, a system and method for generating a highly amplified radio signal comprising extremely low frequency or very low frequency radio signals for feedback into the human body for therapeutic purposes.

2. Discussion of Related Art

The present invention described herein is based on the early work of Snape, d'Arsonval, Rabinovitch, and Leduc. In particular, Snape pioneered the use of extremely low radio frequencies (ELF) as an anesthetic in dental extraction (Snape, J., On electricity as an anesthetic in dental extractions, Trans. Odont. Soc. Gr. Brit., pp. 287–312. (1869)). Subsequently, in 1890, Arsine d'Arsonval demonstrated that ELF pulsed electrical currents, ranging from 2500 Hz to 10,000 Hz, induced general anesthesia in humans. Similarly, in 1902, Leduc demonstrated that a pulsed electrical DC current applied to the central nervous system could effectively induce anesthesia. Rabinovitch did extensive work in the area of electric analgesia sleep and resuscitation (Rabinovitch, L. G., Electric Analgesia Sleep and Resuscitation Anesthesia (chap. XVI), ed. J. T. Gwatheny. D. Appleton & Co., New York, pp. 628–643 (1914)). More recently, Czaja demonstrated that treatment in the ELF frequency range enhances the immune system (Czaja, W., Comparative Studies of Electro-analgesia and Barbiturates, Polski Archirum Weterynaryjne, pp. 205–224 (1986)).

Between 1965 and 1973 Applicant demonstrated that antennae sensilla on insects act as photonic waveguides to collect and transmit infrared frequencies. From this early research, Applicant postulated that living systems (e.g., insect spines and plant fibers) also utilize the radio portion of the frequency spectrum to energize photons from radio and infrared emitting molecules. The requirement for detecting and or stimulating infrared and radio emissions from living systems is the ELF modulation of the organic and gaseous interface located at the waxy surface of the system. That is, living systems store coherent photon emissions from the external environment which become part of the self-organization of the living system. It has been demonstrated that ELF frequencies in living systems range from $10^3$ Hz in nerve action potentials to $10^{-2}$ Hz for physiological functions.

Based on these principles, Applicant has determined that radio waves in the ELF region of the radio spectrum are propagated along the atmospheric boundary layer of the human skin. ELF in the range of 800 Hz to 5200 Hz averaging 1000 Hz, with narrowband 10,000 Hz to 150,000 Hz sideband ELF radio signals are natural to the skin surface. The 700 Hz to 10,000 Hz region of the frequency spectrum is the region of so called radio "whistlers" (i.e. radio signals) from atmospheric lightning strikes around the world. It is this atmospheric electricity that modulates the frequencies from the atmospheric boundary layer of the skin. These modulation frequencies are equivalent to the 3 Hz to 40 Hz oscillations discovered by W. O. Schumann stimulated by lightning. These flicker modulations (which are approximately 3 Hz to 6 Hz) can be observed on an oscilloscope while measuring the 1000 Hz and 10,000 sidebands present on the human skin.

In 1952, Schumann calculated the atmospheric cavity resonance between the earth and ionosphere as being in the low ELF region (e.g., 1 to 40 Hz). In 1962 H. L. Koening measured these photonic radio waves and pointed out that some of them fall in the same region as human EEG frequencies between 0.5 and 3 Hz. In 1974 M. A. Persinger found ELF field effects on mammals and persons. A summary of the therapeutic effects of ELF is given in Ehrmann et al., "Influence of Altering Magnetic Fields [Frequencies Between 1 and 20 Hz] on Psychosomatic Ailments", presented at the second Bioclimatological Colloquium (1976).

The above work deals with the effect of radio frequencies on the diseased body. However, these articles do not consider the modulation of waves by lower frequencies or the wave form of the treatment frequencies. Nor do they contemplate a specific environment for applying radio frequencies to the diseased body for therapeutic purposes.

BRIEF DESCRIPTION OF THE INVENTION

These and other advances concerning electricity and its effect upon living systems, as well as the discovery that radio waves in the ELF region are propagated along the atmospheric boundary layer of the human skin are utilized by the present invention. The present invention includes an apparatus and method for generating the biophotonic radio frequencies that propagate along the atmospheric boundary layer of the human skin. The present invention further includes a method and apparatus for using these radio frequencies for therapeutic purposes. In addition, exact human-atmospheric, stone, sand, and plant frequency ranges, their modulation parameters, and their exact waveforms are elucidated herein.

These functions are realized with the use of a series of oscillators (i.e., electronic function generators) designed to produce modulated sine wave and square-like wave photons wave photons. The oscillators are further adapted to emit the modulated sine and square wave photons from a dielectric or metal antenna built as loops into the walls of a diamagnetic-paramagnetic chamber. When a person is seated in the chamber, the photons of energy from the waves generated along the loop antenna penetrate the human body and provide a variety of therapeutic effects. Among these therapeutic effects are relief of rheumatic muscular pain, slowing the metabolism, increasing the efficiency of the immune system, eliminating certain psychosomatic ailments, and suppressing cancer.

BRIEF DESCRIPTION OF THE DRAWING AND SPECTRUM

The foregoing and other objects, features and advantages of the invention will be apparent from tile following more particular description of the preferred embodiments of the invention, as illustrated in the accompanying drawings in which:

FIG. 1 (A) shows a front view of a treatment chamber constructed in accordance with the present invention.

FIG. 1 (B) shows a top view of the treatment chamber.

FIGS. 2(A) and 2(B) show a detailed block diagram of a wave generator constructed in accordance with the present invention.

FIGS. 3(A) through 3(G) illustrate eight different exemplary signals that can be produced and used within the treatment chamber for therapeutic purposes.

FIG. 4 illustrates a soliton group wave.

DESCRIPTION OF THE PREFERRED EMBODIMENTS

Radio waves in the Extremely Low Frequency (ELF) and Very Low Frequency (VLF) region are propagated along the atmospheric boundary layer of the human or mammalian skin, rock surfaces, sod (soil), and plants (in particular trees). These radio waves occur between 0.5 Hz and 20,000 Hz in the Schumann, electrical anesthesia, and electronic induction portion of the electromagnetic spectrum. Furthermore, these radio waves sometimes show narrow 10,000 Hz to 20,000 Hz narrow sidebands that vary from person to person, plant to plant, etc., due to the health of the living animal or plant, the time of day, and the weather conditions. The highest peak of these emissions occurs at dawn and dusk (i.e. between 0630 to 0930 hrs and from 1830 to 2130 hrs). In other words, these radio waves tend to increase in amplitude during these peak dawn and dusk times.

Figure 1A:
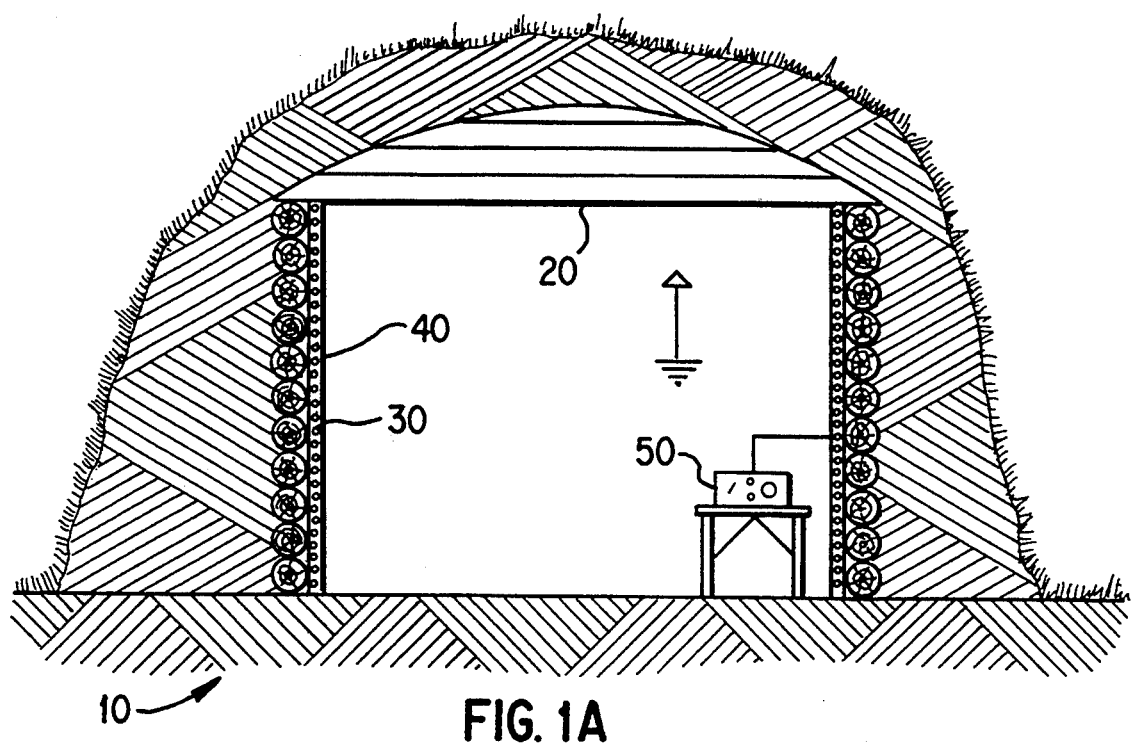
Figure 1B:
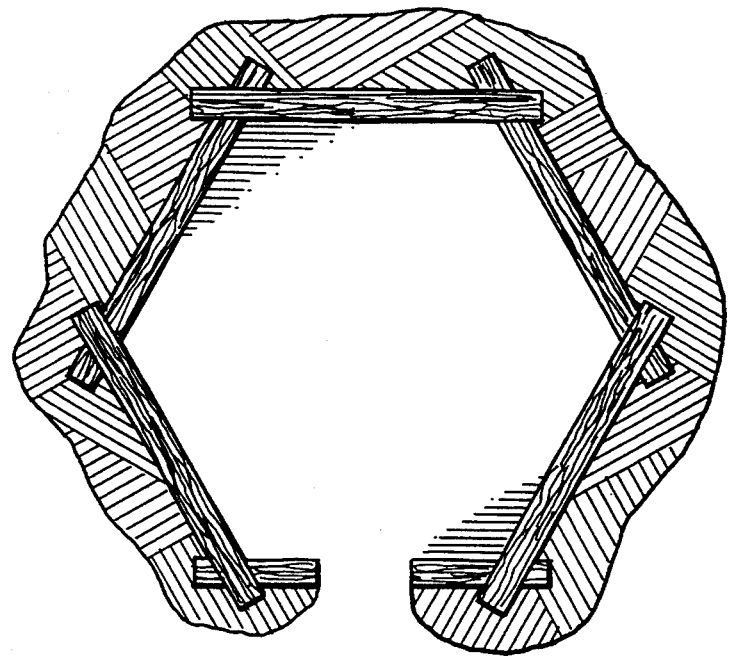

FIG. 1(A) shows a front sectional view of a treatment chamber 10 constructed in accordance with the present invention. FIG. 1(B) shows a top sectional view of the treatment chamber 10. The treatment chamber 10 is built in a hexagon shape of Navajo hogan design. The treatment chamber can be built to any dimensions so long as a human can comfortably sit in the treatment chamber 10 without making contact with the walls of the treatment chamber 10. A recommended size is 8 feet by 8 feet. In a preferred embodiment, the treatment chamber 10 is made of wooden logs or architect square logs each of which are approximately six inches thick. Wood is used because it is an excellent diamagnetic material (i.e., it is repelled by a magnetic field). In other words, the treatment chamber 10 is constructed from a material that helps insulate the patient sitting in the treatment chamber 10 from outside magnetic forces.

The treatment chamber 10 has a roof 20 constructed from corbled logs and/or wood. The entire treatment chamber 10 is covered with paramagnetic earth (200 centimeter-grams, per second (cgs) or above—cgs defined generally as the amount of time one gram of a material will move towards a magnet placed one centimeter away). The earth mound is sodded with a living grass. The treatment chamber 10 could also be covered with bricks instead of earth so long as the bricks are paramagnetic. In other words, the treatment chamber can be covered by any material that is paramagnetic. The floor of the treatment chamber 10 is constructed from hardened compact clay or earth. The floor is also covered with a wool carpet 95 since wool does not store a magnetic charge.

The configuration of the treatment chamber 10 provides a layered system since the earth covering is paramagnetic and the wood is diamagnetic. In this document the term paramagnetic is defined as a material that is susceptible to magnetism. The material does not store the magnetic force, rather if brought in contact with a magnet it would be drawn towards it. Diamagnetic is the opposite. A diamagnetic material is repelled by a magnet. Diamagnetic materials also do not store a magnetic force.

Experiments by the Applicant in volcanic areas with paramagnetic soil (e.g., Ireland) and in diamagnetic areas with little or no soil (e.g., Upper Amazon) have shown that a combination of a diamagnetic layer (e.g., plant material) and a paramagnetic layer (e.g., volcanic earth or clay brick) tend to focus or concentrate the radio waves (describe below) that are introduced into the treatment chamber 10. It appears that diamagnetic-paramagnetic layers act as a condenser for storing and discharging the ELF and VLF energy.

An antenna loop 30 is imbedded in the wall of the treatment chamber 10. The antenna loop 30 is formed from thin copper wire or of ¼ inch hemp rope which has been soaked for one day in a sea salt solution. Other materials that could be used to construct the antenna loop would be apparent to a person skilled in the relevant art.

The antenna loop 30 encircles the treatment chamber 10 within a diamagnetic fiberboard wall 40. The antenna loop 30 is spaced with the individual loops one inch apart from floor to ceiling.

Figure 2A:
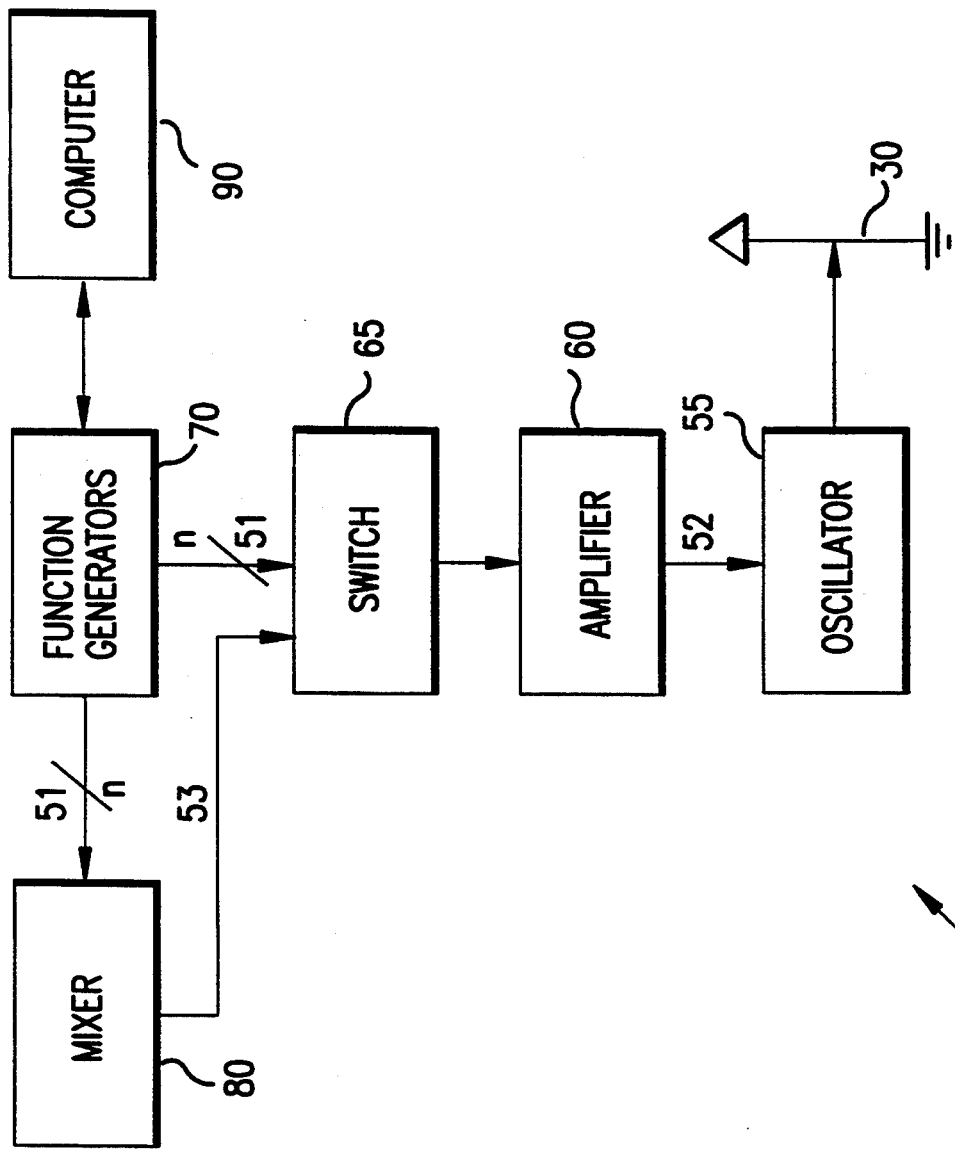
Figure 2B:
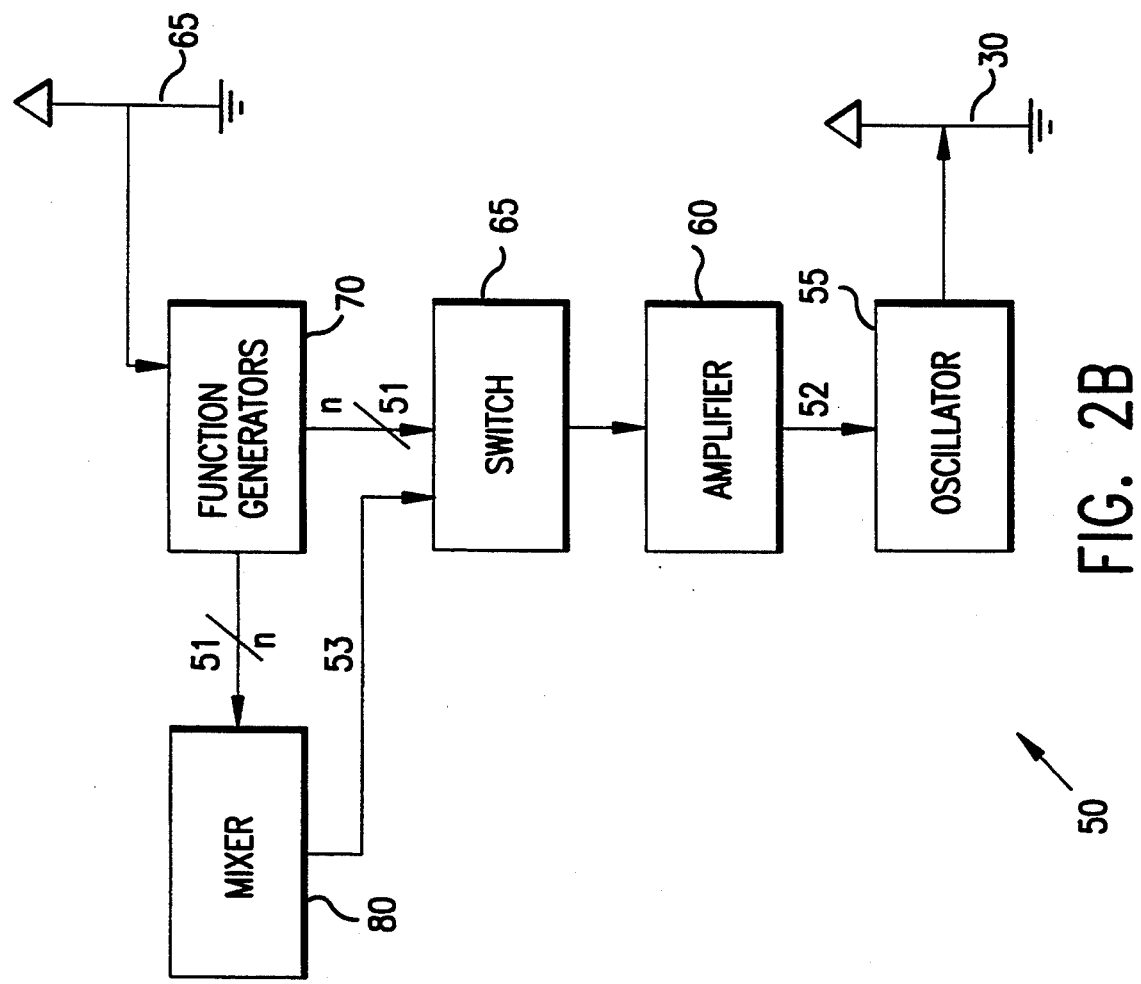

The leads from the antenna loop 30 are passed through the fiberboard wall 40 and connected to a wave generator 50. FIG. 2 shows a block diagram of the wave generator 50. The wave generator 50 includes an oscillator 55 (oscillator 55 is also referred to as a function generator), an amplifier 60, an arbitrary function generator 70, a mixer 80, and a computer 90. Each of these components will now be described in detail.

The arbitrary function generator 70 is controlled by the computer 90. The arbitrary function generator 70 is an instrument which generates periodic waveforms that duplicate various types of defined mathematical functions. In other words, the arbitrary function generator 70 is computer programmable to duplicate any known frequency or waveform. Function generators are well known in the art, and for the sake of brevity, the programming and operation of the arbitrary function generator 70 will not be described in detail here. In operation, a user programs the computer 90 to provide a particular waveform to the arbitrary function generator 70. The arbitrary function generator 70 duplicates the waveform provided by the computer 70 and produces waveform S1.

In an alternate embodiment, an antenna 65 is connected directly to the arbitrary function generator 70. As discussed above, there are a variety of radio waves that are natural to the atmosphere. The present invention is based on the theory that these natural waves, if applied in an amplified form to the human body, can provide therapeutic benefits. Thus, the antenna 65 can be connected directly to the function generator 70, which in turn duplicates the exact waveform of the radio waves that are propagating within the atmosphere. The preferred antenna used for detecting these natural radio waves can be found in a patent application filed Apr. 19, 1993, in the name of Dr. Philip S. Callahan, entitled "Photonic Ionic Cord Detector of Group Waves" U.S. patent application Ser. No. 08/047,486, which is hereby incorporated by reference in its entirety.

The arbitrary function generator 70 is connected to the amplifier 60. Amplifiers are very well known, and for the sake of brevity a detailed description of the amplifier 60 will not be given. The amplifier 60 amplifies the waveform S1 produced by the arbitrary function generator 70. The amplifier 60 produces amplified waveform S2. The amplifier 60 is connected to the oscillator 55 which stabilizes the amplified waveform S2. Note that the amplifier 60 can be connected directly to the antenna 30, but the waveform might not be as stable.

The oscillator 55 is connected to the antenna 30. Thus, the duplicated amplified waveform is provided to the antenna 30. These waveforms are transmitted into the treatment chamber 10 by the antenna 30. It is these waveforms that provide therapeutic benefits.

The waveform S1 can take many forms, including a sine wave or a sine wave riding another sine wave. The first signal S1 is typically a modulated millivolt signal. The modulated millivolt signal is amplified by the amplifier 60 up to volt ranges.

It has been determined by Applicant that the natural radio waves that propagate throughout the atmosphere, as well as the natural waves that propagate along the surface of the human body if amplified and provided to a diseased body can aid in the treatment of diseases or medical ailments. Consequently, it is these natural radio waves that should be duplicated and generated by the arbitrary function generator 70. Some of these waveforms are described briefly below.

FIGS. 3(A) through 3(H) illustrate eight different exemplary waveforms (i.e., radio waves) that can be produced by the arbitrary function generator 70. All eight radio waves occur naturally in the atmosphere or along the surface of the human body. The computer 90 is programmed by a user to generate the desired waveform. Such programming would be apparent to a person skilled in the relevant art based on the following description of exemplary waveforms. As discussed above, this waveform is duplicated by the arbitrary function generator 70. These signals are described briefly below.

Figure 4A:
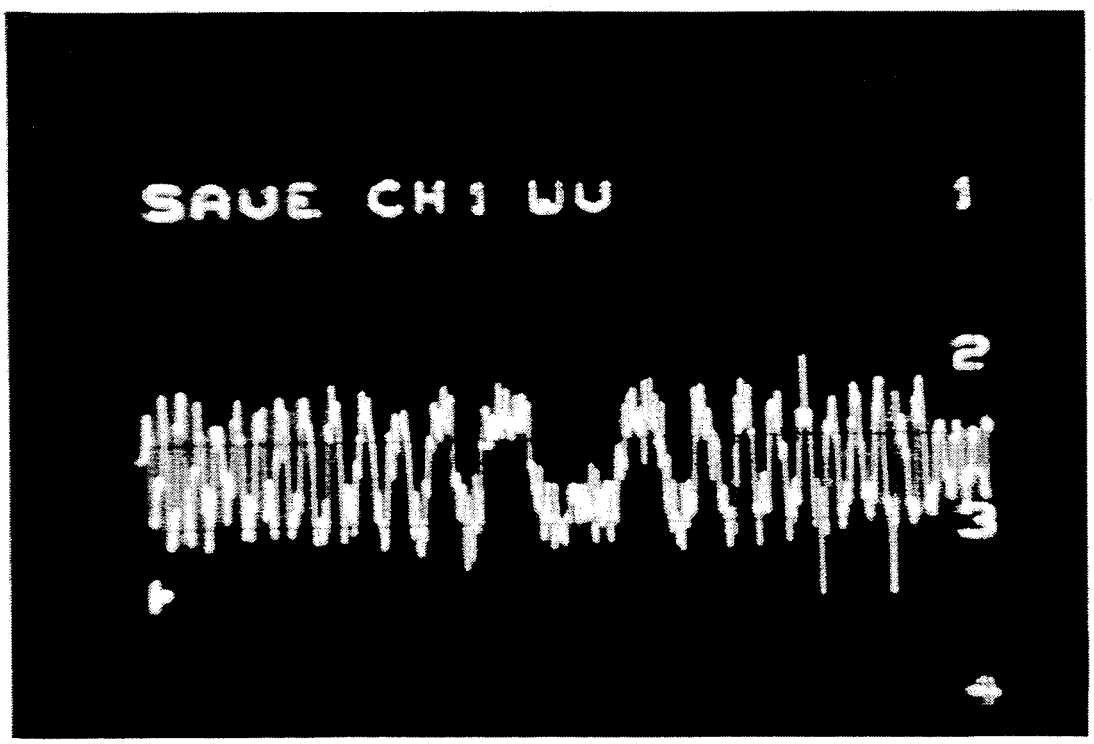
Figure 4B:
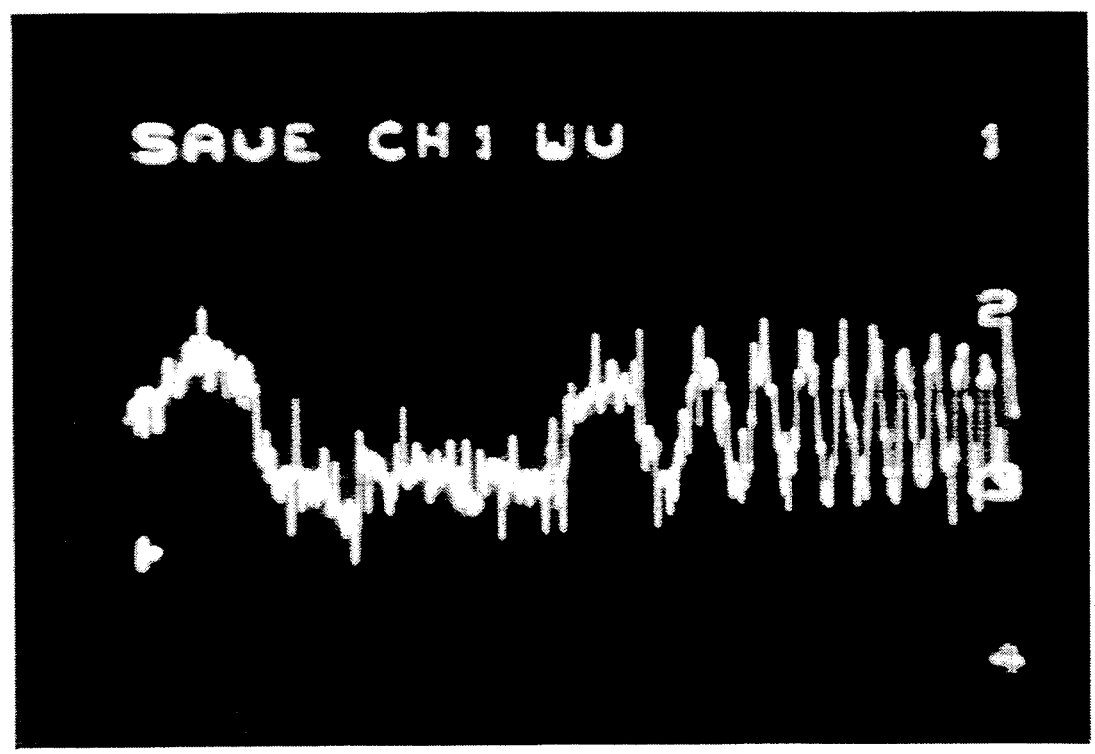

FIG. 3A illustrates an unmodulated waveform. The unmodulated waveform can have resonant peaks at 4, 8, 14 or 28 Herts (Hz). FIG. 3B illustrates a modulated 2,000 Hz sine wave carried on a 4 to 8 Hz sine wave. FIG. 3C illustrates a modulated 100 Hz sine wave carried on a 4 Hz sine wave. FIG. 3D illustrates a modulated 600 Hz square wave carried on a 120 Hz sine wave. FIG. 3E illustrates a modulated 8700 Hz sine wave with 20,000 Hz spikes generated and carried randomly along its fixed frequency. FIG. 3F illustrates a modulated 600 Hz grounded square wave with 20,000 Hz spikes generated and carried randomly along its fixed frequency. FIG. 3G illustrates a soliton target or group waves, of a very specific form, varying between 0.5 Hz and 1000 Hz with a band gap of between 1 Hz and 10 Hz in the middle as given in FIG. 4.

A group wave is the sum of many phase waves. For a more derailed discussion of group waves see Brillouin and Sommerfield, Wave Propagation and Group Velocity, Academic Press, New York, 1960. These radio waves have been so named because the varying group wave frequencies modulate a basic phase Schumann wave. Note that Schumann waves vary with geographic region. Since a soliton is a wave riding another wave and the varying group wave between 0.5 Hz to 170 Hz is superimposed (frequency modulates) on the standard geographical Schumann wave. The soliton is considered by Applicant to be a special sum group (sometimes called target waves) of the natural unpolluted atmosphere. (See Allowiz and Segur, Solitons and Inverse Scattering Transform, Siam Publishers, Philadelphia, 1981.) The radio group soliton waves have recently been discovered by Applicant in nature. In a preferred embodiment, the wave generator 70 is programmed by computer 90 to duplicate and generate the soliton group wave (see FIG. 4) since Applicant believes this wave provides the most beneficial therapeutic effects.

The amplifier 60 may be connected to a plurality of arbitrary function generators 70 each producing a different waveform S1. A first switch 65 is provided so that one of the signals S1 or a mixed signal S3 can be selected and fed into the amplifier 60. A second switch (not shown) is provided to allow multiple waveforms S1 to be input into the mixer 80.

The mixer 80 is capable of producing a variety of different signals that are deviations from the waveforms S1. Note that if the mixer 80 is used the first switch (not shown) does not select a waveform S1 from the arbitrary function generators 70. The mixer 80 emits single or mixtures of the duplicated waveforms emitted by the arbitrary function generators 70. This mixed waveform is labeled S3. The emitted waveform S3 from the mixer 80 is provided to the amplifier 60. Note that the signals from the arbitrary function generators 70 do not have to pass through the mixer 80. Rather the signals from the arbitrary function generator 70 can be, and most frequently are, passed directly to the amplifier 60.

The treatment chamber 10 should be located at least ½ mile from an AC power source (60 Hz or greater). The wave generator 50 should be DC battery operated.

The preferred means for the patient to absorb the therapeutic frequencies is to sit in the center of the treatment chamber 10 without contacting the surrounding loop antenna (i.e., without contacting the surrounding walls of the treatment chamber). Thus, only the atmospheric-skin boundary frequencies emitted by the loop antenna 30 are absorbed by the patient. The wave generator 50 is tuned depending on the specific therapeutic treatment. The tuning of the wave generator 50 is based on previously proven wave forms (see Ehrmann cited above), or by experimentation.

In short, the treatment chamber 10 is imitating nature but in a more amplified manner. By providing an environment that contains an atmosphere that is saturated with amplified radio signals that are natural (i.e., propagate within the earths atmosphere or along the surface of the human body), the patient can obtain a significant therapeutic benefit.

An alternate method of using the teachings of the present invention is to feed the radio waves that are output from the antenna 30 directly into the human body by grounding the feet and placing the antenna lead in one hand of the patient.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A treatment chamber, comprising:
   (1) a chamber having a floor and a plurality of walls constructed from a diamagnetic material, wherein said chamber is covered with a paramagnetic material;
   (2) an antenna that is embedded in at least one of said plurality of walls of said chamber;
   (3) a wave generator, electrically coupled to said antenna, that produces a waveform, wherein said wave generator includes, (a) at least one electromagnetic function generator adapted to duplicate a predetermined waveform, (b) an amplifier, electrically coupled to said at least one electromagnetic function generator, that produces an amplified waveform by amplifying said duplicated waveform produced by said at least one electromagnetic function generator, and (c) an oscillator, electrically coupled to said amplifier, adapted to duplicate said amplified waveform, whereby said wave generator produces ELF and VLF radio frequencies and emits them via said antenna into said chamber for absorption by the atmospheric-skin boundary layer of the human skin.

2. The system of claim 1, further comprising mixing means for producing a mix of the waveforms produced by said at least one function generator.

3. The treatment chamber of claim 1, wherein said said floor of said chamber is constructed from hardened clay.

4. The treatment chamber of claim 3, further comprising a wool carpet, wherein said wool carpet covers said floor.

5. The treatment chamber of claim 1, wherein said antenna is constructed from hemp that has been soaked in a salt solution.

6. The treatment chamber of claim 1, wherein said antenna encircles said treatment chamber within said plurality of walls.

7. The treatment chamber of claim 1, wherein said electromagnetic function generator emits 4, 8, 14 and 18 Hz sine waves.

8. The treatment chamber of claim 1, wherein said electromagnetic function generator emits a 4 Hz sine wave modulating a 2,000 Hz sine wave carrier.

9. The treatment chamber of claim 1, wherein said electromagnetic function generator emits a 4 Hz sine wave modulating a 100 Hz sine wave carrier.

10. The treatment chamber of claim 1, wherein said electromagnetic function generator emits a 120 Hz sine wave modulating a 600 Hz square wave.

11. The treatment chamber of claim 1, wherein said electromagnetic function generator emits a 8,700 Hz sine wave with 10,000 Hz spike emitted along its length.

12. The treatment chamber of claim 1, wherein said electromagnetic function generator emits a 600 Hz sine wave with a 10,000 Hz spike emitted along its length.

13. The treatment chamber of claim 1, wherein said electromagnetic function generator emits soliton waves of changing narrow band to gradually expanding wider band ELF frequencies with a 1 to 10 Hz band gap between the changing frequencies.

14. The treatment chamber of claim 1, wherein said electromagnetic function generator emits a 8 Hz sine wave modulating a 2,000 Hz sine wave carrier.

15. The treatment chamber of claim 1, wherein said electromagnetic function generator emits a 8,700 Hz sine wave with a 20,000 Hz spike emitted along its length.

16. The treatment chamber of claim 1, wherein said electromagnetic function generator emits 600 Hz sine waves with a 20,000 Hz spike emitted along its length.

17. A method of treating a patient for a particular medical ailment, comprising the steps of:

(1) placing the patient within a treatment chamber constructed from a diamagnetic material and covered with a paramagnetic material; and (2) applying a biophotonic amplified waveform to the patient via an antenna that is embedded in the wall of said treatment chamber, wherein said biophotonic amplified waveform is a duplicate of a waveform that propagates naturally either along the atmospheric boundary layer of the human skin or within the atmosphere of the earth;

whereby the patient absorbs said biophotonic amplified waveform through the atmospheric-skin boundary layer of the human skin and is thereby provided with a therapeutic benefit.

18. The method of claim 14, further comprising the step of producing a soliton group wave, wherein said biophotonic amplified waveform is said soliton group wave.

* * * * *